United States Patent [19]

Gold et al.

[11] 4,244,798

[45] Jan. 13, 1981

[54] EXHAUST ELECTRODE PROCESS FOR EXHAUST GAS OXYGEN SENSOR

[75] Inventors: Terry J. Gold, Flint; Frederick L. Kennard, III, Holly; Paul C. Kikuchi; Ralph V. Wilhelm, Jr., both of Flint, all of Mich.

[73] Assignee: General Motors Corporation, Detroit, Mich.

[21] Appl. No.: 89,264

[22] Filed: Oct. 29, 1979

Related U.S. Application Data

[63] Continuation-in-part of Ser. No. 030,775, Apr. 17, 1979, abandoned.

[51] Int. Cl.$^3$ .............................................. C23C 15/00
[52] U.S. Cl. ........................... 204/192 SP; 204/195 S
[58] Field of Search ........... 204/192 C, 192 SP, 195 S

[56] References Cited

U.S. PATENT DOCUMENTS

| | | | |
|---|---|---|---|
| 3,844,920 | 10/1974 | Burgett et al. | 204/195 S |
| 3,978,006 | 8/1976 | Topp et al. | 252/477 R |
| 4,021,326 | 3/1977 | Pollner et al. | 204/195 S |
| 4,116,883 | 9/1978 | Rhodes | 252/463 |
| 4,129,848 | 12/1978 | Frank et al. | 338/308 |
| 4,136,000 | 1/1979 | Davis et al. | 204/195 S |

*Primary Examiner*—Howard S. Williams
*Assistant Examiner*—William Leader
*Attorney, Agent, or Firm*—Robert J. Wallace

[57] ABSTRACT

A method of sputtering a platinum exhaust gas electrode onto a vitrified zirconia thimble for an electrochemical-type exhaust gas oxygen sensor. Porous high surface area platinum films are deposited that have more consistent properties. A platinum target is spaced about 3.0–4.5 cm from the thimble and more than 6 cm from the sputtering anode. A pressure of about 10–20 millitorr is used during sputtering at a DC power of about 13–22 watts/cm$^2$ of target area.

3 Claims, No Drawings

EXHAUST ELECTRODE PROCESS FOR EXHAUST GAS OXYGEN SENSOR

RELATED PATENT APPLICATION

This patent application is a continuation-in-part of United States patent application Ser. No. 030,775, filed Apr. 17, 1979, now abandoned and entitled "Exhaust Electrode Process for Exhaust Gas Oxygen Sensor".

FIELD OF THE INVENTION

This invention relates to solid electrolyte, electrochemical-type exhaust gas oxygen sensors. It more particularly relates to a sputtering process for depositing a platinum exhaust electrode onto vitrified zirconia thimbles for such sensors.

BACKGROUND OF THE INVENTION

A typical automotive-type solid electrolyte exhaust gas oxygen sensor is disclosed in U.S. Pat. No. 3,844,920 Burgett et al. It has a zirconia sensing element shaped as a tapered thimble. One end is open and has a circumferential flange. The other end is closed, and forms the most active part of the element. The interior and exterior of the thimble have separate porous electrode coatings of platinum or the like. The inner electrode is exposed to a source of oxygen, such as air or a mixed metal oxide, for establishing a reference potential. This electrode has generally been formed by painting a coating of a platinum ink onto the zirconia thimble, drying the coating, and then firing the coated thimble at an elevated temperature. An improved technique by which it can be applied is described and claimed in United States patent application Ser. No. 089,264 entitled "Reference Electrode Process for Exhaust Gas Oxygen Sensor", filed on Oct. 1, 1979 in the name of John Trevorrow and assigned to the assignee of this invention.

The outer electrode is exposed to the exhaust gas for establishing a potential determined by exhaust gas oxygen concentration. The outer electrode can be a porous thick film of platinum, like the inner electrode. However, it is preferred that this outer electrode be a thin film, applied by evaporation, sputtering, chemical vapor deposition or other such thin film deposition techniques. On the other hand, it has been difficult to consistently reproduce desirable properties, such as porosity and electrical parameters, in the thin film electrodes. As a result, yields of satisfactory electrode properties have been limited, and various ancillary procedures have been developed to improve them. For example, U.S. Pat. No. 3,978,006 Topp et al discloses heating the solid electrolyte body after electrode deposition, to form pores in the electrode coating if it is not porous as deposited. U.S. Pat. No. 4,136,000 Davis et al discloses treating the electroded sensor element chemically and electrolytically to enhance sensor properties. Moreover, it is known that zirconia-type exhaust gas sensors, particularly those with a sputtered exhaust gas electrode, are likely to change electrical characteristics after a short time in operation. Generally, there is an improvement, such as a reduction in switching response time. Consequently, it has been proposed to operate such sensors functionally in an actual or simulated exhaust gas stream until they are sufficiently stabilized, before installing them in an actual working system. Such treatments, of course, add to the cost of manufacture. Moreover, the yield of higher performance sensors is still inherently limited by the quality of the electrode film originally deposited. We have found how to sputter platinum films onto the zirconia surface in such a manner that the film is consistently porous as deposited and has a consistently high surface area as deposited, which contributes to a greater yield of high quality sensors. Sensors with low lean-to-rich switching response times are produced, without post-electroding treatments. Rich-to-lean switching response times are initially not nearly as low as lean-to-rich switching response times. However, they are generally readily reduced to acceptably low levels after only a short actual or simulated aging. Hence, a high yield of significantly fast sensors is obtained from only minimal actual aging. In fact, sensors with exhaust electrodes produced in accordance with this invention are susceptible to aging by a simple furnace treatment, as is disclosed and claimed in United States patent application Ser. No. 030,747 entitled "Aging Treatment for Exhaust Gas Oxygen Sensor", filed on Apr. 17, 1979 herewith in the names of Morris Berg, Slater W. Hawes, Frederick L. Kennard, III and Paul C. Kikuchi and assigned to the assignee hereof. In addition, a sizeable proportion of sensors having exhaust electrodes produced with this invention do not even need any post-electroding treatments for activation or stabilization. Their electrical properties as formed are more than adequate and remain substantially stable during initial sensor use.

OBJECTS AND SUMMARY OF THE INVENTION

An object of this invention is to provide an improved sputtering process for depositing a platinum exhaust electrode onto a zirconia solid electrolyte body for an electrochemical-type exhaust gas oxygen sensor.

The invention comprehends sputtering platinum onto a vitrified zirconia solid electrolyte body which is widely spaced from the platinum target. The target is more than about 3.7 centimeters away from the workpiece, in a preferred example. The platinum is DC sputtered from the target under a relatively high pressure of about 10–20 millitorr and a sputtering power of about 13–22 watts/cm$^2$ of target area.

DESCRIPTION OF THE PREFERRED EMBODIMENTS

Vitrified zirconia thimbles the same as described in the aforementioned United States patent application Ser. No. 089,264, can be exteriorly coated in accordance with this invention. These thimbles are about 3–5 cm long and are of zirconia partially or fully stabilized in its cubic form by the inclusion of about 4–8 mole percent yttria. Each thimble has a taper on its outer surface of about 3 degrees-38 minutes. In a particular example, it has an axis length of about 3.66 cm. Its wider end has a circumferential shoulder and a diameter about 0.82 cm immediately below the shoulder. Its narrower end is closed and rounded, having an external spherical radius of curvature of about 3 mm. Its diameter adjacent the rounded end is about 0.4 cm. We believe it is important to control deposition on and near the rounded end tip. This appears to be the most active part of the sensing element. The inner electrode is formed on the thimbles first. We prefer it to be a platinum ink thick film fired to the zirconia surface, and preferably applied by the coating process described in the aforementioned Ser. No. 089,264. The thimbles are then cleaned to receive the thin film outer exhaust electrode in accordance with this invention.

As is usual for any thin film deposition process, the zirconia surface should be well cleaned before depositing the platinum electrode onto it in accordance with this invention. We expect that any normal and accepted high quality cleaning procedures can be used. One cleaning procedure that can be used includes ultrasonically degreasing the zirconia with freon, and then heating it to about 600° C. in air for about an hour. The zirconia thimbles are then placed on a stainless steel pallet, and the pallet placed in a vacuum chamber. The vacuum chamber is then pumped down to a pressure of approximately 100 millitorr. While at or below this low pressure, the zirconia thimbles are heated again, to a temperature of about 200° C. for about 10-15 minutes. while the zirconia thimbles are still warm, the vacuum chamber is backfilled with dry nitrogen to greater than 1 torr in about 1 second. The chamber is then immediately pumped down again to a pressure below $2 \times 10^{-6}$ torr. A flow of argon at about 75-100 cc per minute is then started through the vacuum chamber while pumping continues. The flow of argon and the pumping continues and the vacuum valving is adjusted until pressure equilibrates at about 10-20 millitorr. This argon pressure is similarly dynamically maintained during the sputtering process. Chamber atmosphere is thus continually refreshed during sputtering. In our process we can simultaneously sputter electrode films onto large groups of such zirconia thimbles such as over 200 thimbles. The pallet with its thimbles is placed directly on a horizontal planar steel pallet carrier. The thimble axes are parallel to each other and oriented vertically. Their open ends rest on the pallet. The pallet carrier is disposed about 0.5-1.5 cm above the anode. However, we do not know if any separation is needed at all. The thimble closed ends face upwardly toward a planar platinum target surface of a cathode, which surface is spaced about 3.8 cm above the thimble closed ends. The sputtering target is a platinum sheet bonded to a supporting copper backing plate. The target is assembled with a cathode that includes water cooling means and a magnet array. An argon pressure of 10-20 millitorr is dynamically maintained in the sputtering chamber. A DC voltage of approximately 500 to 800 is applied between the target and the anode. The sputtering power supply is adjusted to provide a DC power between the target and the anode of approximately 13-22 watts/cm² of target area. No special means are used in the pallet, pallet carrier, or anode to heat or cool the thimbles during sputtering.

Sputtering is continued under the above conditions, while maintaining the aforementioned 10-20 millitorr argon pressure, until a platinum weight of about 10 mg is deposited onto each element. This will produce a porous crystalline platinum deposit about 1.0-1.5 micrometers thick on the rounded end, about 0.65-1.0 micrometers thick about 0.5 cm back from that end, and about 0.3-0.75 micrometers thick about 2 cm back from the rounded end. Coating thicknesses such as these are obtained by sputtering for about 3-5 minutes under the foregoing conditions. We believe that electrode porosity and perhaps surface area, and the resultant sensor electrical characteristics are a function of electrode thickness. Also, the temperature that the ceramic self-heats to during deposition is important. The techniques of this invention should provide an apparent electrode surface area at least double its geometric surface area. By apparent surface area, we mean the surface area in the film coated part of the element as determined by conventional gas adsorption techniques. By geometric surface area, we mean surface area as determined from a drawing of the element. In many instances the process of this invention will provide a fourfold increase in apparent surface area as deposited over the underlying zirconia surface, if the latter is not particularly rough. Adhesion of the sputtered film to its underlying zirconia can be increased by heating the electroded element in air for about 1 hour at 800° C. Such a heating does appear to reduce apparent surface area significantly, and may open some large pores in the film, about 0.5-5 micrometers in width. The number and size of these openings appear to depend on the time and temperature of heating and the thickness of the film. The reduction in apparent surface area during this heating does not seem to be significantly detrimental to sensor performance. On the other hand, it seems important that the film have a high porosity and surface area as deposited. Otherwise, sensor performance is adversely affected by this heating.

The electrode film is then preferably given a porous ceramic coating on all its parts except where electrical connection is to be made. The porous ceramic coating can be catalytic or noncatalytic, as desired, without significant initial operating effects on the resultant sensor. For example, it can be a gamma alumina coating prepared and applied as disclosed in U.S. Pat. No. 4,116,883 Rhodes. However, we prefer to flame spray a magnesium-aluminate spinel coating onto the electrode film after the heat treatment to increase electrode adhesion. We recognize that applying the porous overcoating by flame spraying can apparently significantly physically alter the electrode film. However, it nonetheless appears that the essential functional characteristics of the electrode film remain substantially unchanged by the flame spraying. Consequently, the as-deposited characteristics of the electrode film remain fundamentally important.

As previously mentioned, the platinum target, or cathode, is spaced at least about 3.5-4.0, preferably about 3.8 cm above the closed ends of the zirconia thimbles and about 7.6 cm above the anode. This larger than the normal spacing is believed to provide improved electrode porosity and better process controllability. The preferred spacing appears to be critical. If a spacing closer than about 3.0 cm is used between the zirconia closed ends and the target, less porous films appear to result. A spacing greater than about 4.5 cm appears unnecessary and objectionable. It requires higher power settings and argon pressures to obtain a satisfactory coating rate. Platinum deposition in unwanted areas of the apparatus is more likely to occur. Still further, the characteristics of the electrode film are less likely to be reproducible. The nature of the platinum target is no more critical to this invention that it is to any other sputtering of platinum. The target can be obtained from any commercial source, and preferably provides a high purity platinum surface. However, we recognize that in some instances it may prove to be desirable to include minor amounts of other metals in the platinum target along with the pure platinum, as for example, a few percent, up to about 5 percent of palladium and/or rhodium. Because of cost, we prefer a platinum target in which the platinum or platinum alloy is only a surface coating.

A power setting of at least about 13 watts/cm² of target area is required. Lesser power settings apparently result in deposition rates too slow to produce significant porosity and surface area. Conversely, power settings in excess of about 22 watts/cm$^2$ of target area seem to be too severe on system components. Also, the higher power settings may produce platinum deposition in unwanted areas within the vacuum chamber. In any event sensor performance is less reproducible with less than about 13 watts/cm$^2$ of target area. We have found that pressures of about 10–20 millitorr are preferred. This higher pressure range is preferred even though higher power settings are employed. At pressures less than 10 millitorr, the coating appears to be less porous, perhaps because the rate of deposition is too low. At pressures above about 20 millitorr, deposition rate also decreases. Also, deposition may begin to occur on unwanted areas within the vacuum chamber.

The sputtering technique of this invention provides improved electrodes as deposited. For example, lean-to-rich switching response times of less than 600 milliseconds can be consistently produced under commercial production conditions. Rich-to-lean switching response times of less than 1200 milliseconds are consistently produced, as deposited. However, after only a relatively short functioning of an hour or so in exhaust gas the rich-to-lean switching response times consistently drop below 600 milliseconds. Controllability is at about 15 parts air to 1 part fuel, i.e. on the lean side and within about 0.5 air/fuel ratios. Thus, even if the sensor is not fast as formed, it can be consistently operationally aged to provide a fast-acting sensor. Further, the sensor characteristics obtained using electrodes produced by this invention are more reproducible. Higher yields of fast-acting sensors can be obtained by functional aging.

In addition, it has also been discovered that a simple furnace treatment in nitrogen can artificially age sensors having electrodes made in accordance with this invention. The furnace treatment is described and claimed in the aforementioned United States patent application Ser. No. 030,747. DC magnetron sputtering is disclosed herein. However, the principles of this invention should also be applicable to ordinary DC sputtering and to RF sputtering. Still further, the electrode of this invention may be more durable if a platinum cermet stripe is first applied to the outer zirconia surface and fired. If narrow, the stripe need not be porous, and can be of any commercially available platinum ink that adheres well to zirconia when fired, and to which the sputtered platinum deposited over it will adhere.

It should also be noted that platinum was sputtered under an argon atmosphere in the hereinbefore described specific example of this invention. However, as revealed in U.S. Ser. No. 030,748, filed Apr. 17, 1979 in the names of T. J. Gold et al and entitled "Electrode Sputtering Process for Exhaust Gas Oxygen Sensor", an atmosphere predominantly of nitrogen and/or oxygen can be used. Gold et al discloses that such an atmosphere provides significantly improved results over argon when sputtering platinum in accordance with this invention. An atmosphere of 67–75% nitrogen and the balance argon is preferred.

We also wish to note that recent tests indicate the method of this invention may be useful in producing electrodes consisting essentially of palladium. However, it appears that a predominantly nitrogen and/or oxygen sputtering atmosphere is not preferred for sputtering such electrodes, and may even be undesirable.

The embodiments of the invention in which an exclusive property or privilege is claimed are defined as follows:

1. In a method of sputtering a platinum exhaust gas electrode onto a vitrified zirconia solid electrolyte body for an electrochemical-type exhaust gas oxygen sensor, the improvement wherein a platinum target spaced at least 3.0 cm from the body is used in the sputtering, the platinum is sputtered at a pressure of about 10–20 millitorr, and a sputtering power of about 13–22 watts/cm$^2$ of target area is used, whereby the platinum electrode is porous as deposited and has an apparent surface area at least double the geometric area of the zirconia surface on which it lies.

2. In a method of sputtering a platinum exhuast gas electrode onto a vitrified zirconia thimble for an electrochemical-type exhaust gas oxygen sensor, the improvement wherein a generally planar platinum target is oriented normal to the axis of the zirconia thimble and spaced about 3.0–4.5 cm from a closed end on the thimble, the platinum is sputtered using an atmosphere having a pressure of approximately 10–20 millitorr and a DC power of about 13–22 watts/cm$^2$ of target area, whereby the platinum electrode is consistently and reproducibly porous as deposited and has an apparent surface area as deposited at least four times its geometric surface area.

3. In a method of sputtering a platinum exhaust gas electrode onto a vitrified zirconia thimble for an electrochemical-type exhaust gas oxygen sensor, the improvement wherein the thimble is about 3–5 cm long, a generally planar platinum target is oriented normal to the thimble and spaced about 3.5–4.0 cm from a closed end on the thimble, the platinum is DC magnetron sputtered using an atmosphere having a pressure of approximately 10–20 millitorr and a DC power of about 13–22 watts/cm$^2$ of target area and for a duration to produce an electrode thickness of more than about 0.65 micrometer on said end and about 0.3–0.5 micrometer on thimble side walls, whereby the platinum electrode is deposited and has an apparent surface area as deposited at least four times its geometric surface area.

\* \* \* \* \*